United States Patent
Murofushi et al.

[11] Patent Number: 5,972,695
[45] Date of Patent: Oct. 26, 1999

[54] APPARATUS AND METHOD FOR THE PRODUCTION OF XANTHAN GUM

[75] Inventors: Kanji Murofushi; Shigehiro Nagura; Taira Homma, all of Niigata-ken, Japan

[73] Assignees: Shin-Etsu Chemical Co., Ltd., Tokyo, Japan; Shin-Etsu Bio, Inc, San Diego, Calif.

[21] Appl. No.: 08/950,295

[22] Filed: Oct. 14, 1997

Related U.S. Application Data

[63] Continuation of application No. 08/506,787, Jul. 25, 1995, abandoned.

[30] Foreign Application Priority Data

Jul. 26, 1994 [JP] Japan ................................. 6-173035
Dec. 20, 1994 [JP] Japan ................................. 6-316195

[51] Int. Cl.[6] .................................................. C12M 1/02
[52] U.S. Cl. ....................... 435/289.1; 435/101; 435/102; 435/104; 366/295; 366/325.3; 366/325.7
[58] Field of Search ................................. 435/101–104, 435/286.7, 289.1, 818; 422/135, 137, 224, 225, 229; 366/271, 292, 293, 295, 314, 315, 317, 318, 319, 320, 322, 330.1, 325.1, 325.3, 325.7, 325.8

[56] References Cited

U.S. PATENT DOCUMENTS

| | | | |
|---|---|---|---|
| 224,117 | 2/1880 | Ulmer | 366/325.8 |
| 2,740,696 | 4/1956 | Longwell | 422/135 |
| 3,295,834 | 1/1967 | Bendle | 366/325.7 |
| 3,382,229 | 5/1968 | Patton et al. | 435/104 |
| 4,022,438 | 5/1977 | Shishido et al. | |
| 4,243,636 | 1/1981 | Shiraki et al. | 422/135 |
| 4,289,854 | 9/1981 | Tolbert et al. | 435/289.1 |
| 4,472,063 | 9/1984 | Eickelmann | |
| 4,840,905 | 6/1989 | Kearns et al. | 435/289.1 |
| 5,188,808 | 2/1993 | Lilja et al. | |
| 5,248,485 | 9/1993 | Lilja et al. | |

FOREIGN PATENT DOCUMENTS

| | | | |
|---|---|---|---|
| 0316449 | 5/1989 | European Pat. Off. | |
| 1571582 | 6/1969 | France | |
| 3246936 | 6/1984 | Germany | |
| 55-127429 | 10/1980 | Japan | 422/135 |
| 63-283742 | 11/1988 | Japan | 422/135 |

OTHER PUBLICATIONS

Patent Abstracts of Japan, vol. 107, No. 216, Apr. 28, 1993 & JP 04356196–(Shin–Etsu Chemical Co. Ltd.) Dec. 9, 1992.

*Primary Examiner*—William H. Beisner
*Attorney, Agent, or Firm*—McAulay Nissen Goldberg Kiel & Hand, LLP

[57] ABSTRACT

A fermenter for the production of xanthan gum is provided with an upper helical impeller and a lower turbine impeller which are positioned therewithin, and an agitator shaft for driving these helical impeller and turbine impeller. The helical impeller consists of a pair of vertically spaced arms extending from the agitator shaft in opposite directions and arranged in twisted relationship, and at least one shearing paddle bridging these arms, and the turbine impeller consists of a rotating disc having at least one turbine blade attached thereto.

12 Claims, 13 Drawing Sheets

APPARATUS AND METHOD FOR THE PRODUCTION OF XANTHAN GUM

This is a continuation of application Ser. No. 08/506,787, filed Jul. 25, 1995, now abandoned.

1. Field of the Invention

This invention relates to apparatus and method for the production of polymers. In particular, the invention relates to apparatus and a method for the production of polysaccharides from microorganisms using aerobic fermentation methods.

2. Related Art Statement

Polysaccharides produced by microorganisms are generally known as exopolysaccharides and methods for their production, including the parameters for the aerobic fermentation, are known. Typical of these polysaccharides are chitosan, dextran, xanthan gum, gellan gum, welan gum, rhamsan gum, *pullulan,* curdlan, schizophyllan, scleroglucan, levan, and sphingan. See U.S. Pat. No. 5,315,003, and U.S. Pat. application Ser. No. 08/377,440. Perhaps the best known of these polysaccharides is xanthan gum. For the purposes of the invention described herein, the description will be provided in terms of the production of xanthan gum and *pullulan.* However, the invention is equally applicable to other polysaccharides which behave similarly to xanthan gum as described below during their production.

In particular, in xanthan gum fermentation, the product, i.e., xanthan gum, is soluble in the aqueous culture medium, i.e., broth, so that the viscosity of the broth increases with the increased formation of xanthan gum. In the early stage of the fermentation process, good oxygenation of the broth in the fermenter is required to promote growth of the microorganisms. Since this increase in viscosity diminishes the agitating effect and worsens mass transfer within the fermentation chamber, the productivity of xanthan gum is reduced in the later stage of the fermentation. It is desirable to increase the mass transfer as well as the oxygenation as required in the various stages of the process to enhance the productivity and yield of product.

Xanthan gum can be obtained by subjecting an appropriate microorganism, e.g., *Xanthomonas campestris,* which is a xanthan gum-producing bacterium of the genus Xanthomonas, to aerobic fermentation in the presence of appropriate nutrients. The xanthan gum product is dissolved in the broth, the broth is then mixed with isopropanol or another non-solvent for xanthan to cause its precipitation from the broth and the precipitated gum is recovered. (Xanthan gum and its method of production are described in U.S. Pat. No. 3,659,026, column 4.)

Alternatively, xanthan gum-containing fermented solutions can also be prepared by using, in place of *Xanthomonas campestris,* other Xanthomonas bacteria known to be productive of xanthan gum, such as, *Xanthomonas carotate, Xanthomonas incanae, Xanthomonas begoniae, Xanthomonas papavericola, Xanthomonas translucens, Xanthomonas vasculorum* and *Xanthomonas hederae.*

In order to improve aeration and mixing in the fermentation of highly viscous xanthan gum, it is proposed in Japanese Patent Laid-Open Nos. 173795/'86 and 173796/'86 to reduce the viscosity by precipitating xanthan gum as soon as it is formed. However, the microbial cells may be injured by the precipitant or separated from the reaction mixture together with the gum. Moreover, the aforesaid technique usually requires removal of the precipitant from the product, resulting in a considerable increase in cost.

Moreover, it is proposed in Japanese Patent Laid-Open No. 60997/'83 to reduce the viscosity of the fermented solution by emulsion fermentation. However, this technique requires removal of the oil from the product, resulting in an increased cost. A variety of agitation methods have been investigated in connection with the fermentation of xanthan gum and the agitation and mixing of viscous aqueous solutions. Among others, turbine impellers are frequently used in ordinary fermenters because of their high oxygen-dissolving power, and their effectiveness for xanthan gum fermentation and aqueous solutions of xanthan gum has been reported (J. Ferment. Technol., Vol.66, No. 1, pp.103–109, 1988; Chemical Engineering Science, Vol.35, pp.2163–2175, 1980). However, turbine-impellers produce only a radial flow of the fermented solution within the fermenter and fail to create a satisfactory mixed state within the fermenter.

Pullulan is a water-soluble polysaccharide that is produced in a culture solution in the process of cultivating a black yeast called *Aureobasidium pullulans,* a kind of imperfect microorganism, in an aqueous culture medium combining a carbon source, such as, monosaccharides, starch breakdown products and the like with an appropriate nitrogen source. Pullulan has the chemical structure of a linear polymer wherein units of a maltotriose, a glucose trimer having an α-1,4 bond, are repeatedly bonded to each other with an α-1,6 bond.

Industrially, *pullulan* products having a molecular weight of approximately 80,000~300,000 having been manufactured and sold in an large scale and have found a wide application in the food and chemical industries because they are excellent in the characteristics, such as water-solubility, adhesiveness, film-making property and the like. The chemical fields have also used the *pullulan* products as the standard substance to determine the molecular weight of water-soluble macromolecules.

In *pullulan* fermentation, the product, i.e., *pullulan,* is soluble in the aqueous culture medium so that the viscosity of the fermented solution increases with the increased formation of *pullulan.* Since this increase in viscosity diminishes the agitating effect and worsens mass transfer within the fermentation chamber, the productivity of *pullulan* is reduced in the later stage of tie fermentation. This disposition is particularly significant in the fermentation of *pullulan* having the molecular weight of more than 2,000,000.

The macromolecular *pullulan*-producing microorganisms are all bacteria of the *Aureobasidium pullulans* species including variants similar to this species. For example, *Aureobasidium pullulans* that has been deposited in the numbers of IFO6353 and IFO4464 at the Fermentation Research Foundation or in the numbers of ATCC9348, ATCC74100, ATCC74101, ATCC74102, ATCC74103, ATCC74104, ATCC74105, and the like, including their variants, can suitably be used in the practice of the present invention. Of the foregoing bacteria, those of ATCC74100, ATCC74101, ATCC74102, ATCC74103, ATCC74104 and ATCC74105 are particularly suitable as the strains capable of producing macromolecular *pullulan* having the molecular weight of more than 2,000,000 (as described in U.S. Pat. No. 5,268,460).

The culture medium used can contain any ingredients, such as, nitrogen and carbon sources that are usually used in the macromolecular pullulan production and, in the described case, xanthan gum fermentation.

Other agitating elements, such as, marine propellers, helical propellers and pitched-blade impellers, have also been investigated. It is reported that they can produce a vertical flow owing to their inclined blades (Applied Biochemistry and Biotechnology, Vol.28/29, p.667 et seq., 1991; Biotechnology and Bioengineering, Vol.34, pp. 1393–1397, 1989; Chemical Engineering Progress, 1990). However, it is also reported that the combined use of a turbine impeller and any of these agitating elements is disadvantageous from the viewpoint of power consumption (Process Biochemistry, Vol.27, pp.351–365, 15 1992).

Furthermore, it is proposed in Japanese Patent Laid-Open No. 56296/'88 to improve mass transfer within the fermenter by creating a circulating flow with the aid of a pumping system. However, this technique is not desirable in that the system becomes complicated and creates problems with sterilization which is important for purposes of fermentation.

In addition, the results of fermentation carried out without the use of a mechanical agitating element (e.g., processes using a water jet, a bubbling column fermenter or an air lift fermenter) have also been reported. However, none of these processes exhibited sufficient productivity (Biotechnology and Bioengineering, Vol. 39, pp. 85–94, 1992; Appl. Microbiol. Biotechnol., Vol. 35, pp.330–333, 1991).

SUMMARY OF THE INVENTION

Accordingly, it is an object of the present invention to provide an apparatus and method for the production of polysaccharides prepared by aerobic fermentation which can realize a satisfactorily aerated and mixed state of the broth and thereby yield polysaccharide product with high productivity even in the high-viscosity period corresponding to the late stage of the fermentation.

Thus, according to one aspect of the invention, there is provided an agitator component which is a helical impeller comprising:

(1) securement means for connecting the helical impeller to a shaft;

(2) a first pair of arms, each arm of the pair being secured to and extending in the same plane and in opposing directions radially from the securement means, (3) a second pair of arms, each arm of the pair being secured to and extending in the same plane and in opposing directions radially from the securement means, the securement means being adapted to secure the first and second pair of arms on a shaft in a position on the shaft spaced apart from each other and extending from the shaft in a different radial direction from the other so as to define a radial angle therebetween; and (4) at least one shearing paddle having an end connected to one of the first pair of arms and having another end connected to the closest arm of the second pair of arms.

According to another aspect of the present invention, there is provided an agitator for the production of polysaccharides which comprises:

A) a shaft adapted for rotatable mounting in a fermentation chamber having disposed along its length, B) a helical impeller secured to the shaft comprising:
  (1) a first pair of arms, each arm of the pair being secured to and extending in the same plane and in opposing directions radially from the shaft,
  (2) a second pair of arms, each arm of the pair being secured to and extending in the same plane and in opposing directions radially from the shaft,
  the first and second pairs of arms being spaced apart from each other along the length of the shaft and each extending from the shaft in a different radial direction from the other to define a radial angle therebetween; and
  (3) at least one shearing paddle having an end connected to one of the first pair of arms and having another end connected to the closest arm of the second pair of arms; and C) a turbine impeller secured to the shaft at a distal position along the shaft length from the helical impeller, the turbine impeller comprising a rotatable disc having at least one turbine blade extending in a radial direction attached thereto.

According to yet another aspect of the invention, there is provided an apparatus for the production of a polysaccharide using aerobic fermentation of a microorganism comprising:

(A) a fermenter chamber for aerobic fermentation of a culture medium ,
(B) an agitator in the chamber, said agitator comprising:
(1) a vertical shaft rotatably and axially mounted within the chamber,
(2) drive means for rotating the shaft,
(3) a helical impeller secured to the shaft within the fermenter, the helical impeller comprising:
  (a) a first pair of arms, each arm of the pair being secured to and extending in the same plane and in opposing directions radially from the shaft,
  (b) a second pair of arms, each arm of the pair being secured to and extending in the same plane and in opposing directions radially from the shaft, the first and second pairs of arms being spaced apart from each other along the length of the shaft and each extending from the shaft in a different radial direction from the other to define a radial angle therebetween; and
  (c) at least one shearing paddle having an end connected to one of the first pair of arms and having another end connected to the closest arm of the second pair of arms;
(4) a turbine impeller secured to the shaft and positioned vertically below the helical impeller, the turbine impeller comprising a rotatable disc having at least one turbine blade extending in a radial direction attached thereto.

In addition, the present invention provides a method for the production of a polysaccharide gum by using the above-described apparatus, the method comprising the steps of subjecting a culture broth containing a microorganism which produces the desired polysaccharide to aerobic fermentation conditions in the presence of appropriate nutrients so as to cause the microorganism to produce the polysaccharide in the above described apparatus while mechanically agitating and aerating the broth by rotation of the inventive agitator.

An important advantage of the present invention is that the culture broth within the fermenter is agitated by the combined use of a helical impeller and a turbine impeller, thus making it possible to produce xanthan gum by fermentation without causing a reduction in the production rate even in the late stage of the fermentation.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DETAILED DESCRIPTION OF THE PREFERRED EMBODIMENTS

Figure 1:
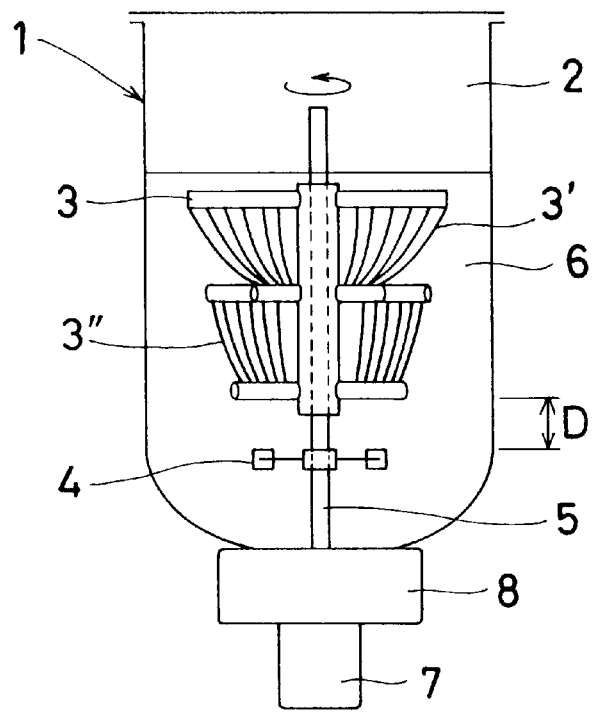
FIG. 1 is a schematic view of one embodiment of an agitator in a fermentation chamber for the production of a polysaccharide in accordance with the present invention.

In a preferred embodiment of the present invention, the radial angle defined between the first and second pair of arms is at least 20 degrees.

Moreover, in the preferred embodiment, the ratio of the diameter of the helical impeller to the tank diameter of the fermenter is not less than 0.5. As used herein, the term diameter when used in reference to the helical impeller means the diameter of a circle defined by the outermost ends of the arms of the helical impeller when rotated about the shaft. The term diameter when used in reference to the fermenter assumes that the fermenter is cylindrical in shape.

Furthermore, in the preferred embodiment, the ratio of the diameter of the turbine impeller to the tank diameter of the fermenter is not less than 0.3. As used herein, the term diameter, when used in reference to the turbine impeller, means the diameter of a circle defined by the outermost ends of the arms of the turbine impeller when rotated about the shaft.

As can be seen from the embodiment which will be described later, the helical impeller used in the present invention is preferably constructed in such a way that it comprises a pair of cylindrical arms positioned perpendicularly to the agitator shaft and a plurality of rod-like shearing paddles bridging and secured to these arms; the upper and lower arms have an angle of twist so as to define a radial angle of not less than 20 degrees when viewed from above.

In the present invention, the inventive agitator comprising the helical impeller and the turbine impeller (which are generally coaxial and attached to a common agitator shaft) are positioned within a fermenter having therein the aforesaid aqueous culture medium containing at least a carbohydrate source and a nitrogen source. For this purpose, there may be used any of various types of fermenter chambers which are well known to those skilled in the art and have been conventionally used.

The xanthan gum-producing microorganisms which can suitably be used in the practice of the present invention are bacteria of the genus Xanthomonas. For example, xanthan gum can be produced by using, in addition to *Xanthomonas campestris* as described above, *Xanthomonas carotate, Xanthomonas incanae, Xanthomonas begoniae, Xanthomonas papavericola, Xanthomonas translucens, Xanthomonas vasculorum* and *Xanthomonas hederae*.

Of the foregoing bacteria, *Xanthomonas campestris* that has been internationally deposited, with accession numbers of ATCC 55298, ATCC 55258, NRRL B-1459 and the like is especially preferred. Of course, if a different polysaccharide is to be produced, the appropriate microorganism will be used. Those skilled in the art are well acquainted with the specific microorganism required for the desired polysaccharide product as well as the conditions and nutrient requirements for the specific organism.

The culture medium used in the present invention can contain any nitrogen and carbon sources that are usually used in the polysaccharide production and in the described case, xanthan gum fermentation. As the nitrogen source, there may used a water-soluble inorganic nitrogenous component such as ammonium salt, a water-soluble organic nitrogenous component such as polypeptone, a water-insoluble organic nitrogenous component such as soybean powder, or the like. The amount of nitrogen source used is in the range of 0.1 to 2.5 g, as nitrogen, per liter.

As the carbon source, there may used one or more compounds selected from sugars, such as, glucose, sucrose, xylose, molasses, starch, maltose and dextrin, and polyhydric alcohols, such as, glycerol and sorbitol. The amount of carbon source used is in the range of 5 to 70 g per liter.

In addition, a phosphate, a magnesium salt and minor component(s) can be used as inorganic salts. As the phosphate, there may be used one or more compounds selected from monopotassium phosphate, dipotassium phosphate, monosodium phosphate, disodium phosphate and the like. The amount of phosphate used is in the range of I to 5 g per liter.

As the magnesium salt, there may be used one or more compounds selected from magnesium phosphate, magnesium sulfate, magnesium nitrate and the like. The amount of magnesium salt used is in the range of 0.1 to 1 g per liter.

As the minor component(s), there may be used one or more compounds selected from ferrous chloride, ferric chloride, ferrous nitrate, ferric nitrate, ferrous phosphate, ferric phosphate, zinc sulfate, zinc chloride, zinc nitrate and zinc phosphate. The amount of minor component(s) used is in the range of 0.02 to 0.08 g per liter.

During fermentation, the ph of the culture medium should preferably be adjusted to 6–8. If the pH is lower than 6 or higher than 8, the productivity of xanthan gum is reduced.

During fermentation, the temperature of the culture medium should preferably be adjusted to 25–35° C. If the temperature is lower than 25° C., the fermentation rate is reduced. If the temperature is higher than 35° C., some of the microbial cells are destroyed which causes a reduction in productivity.

The rate of aeration into the fermenter should preferably be in the range of 0.2 to 1.0 vvm. If the rate of aeration is less than 0.2 vvm, a sufficient amount of oxygen for the growth of microbial cells is not supplied. If the rate of aeration is greater than 1.0 vvm, no further improvement in productivity is produced and it is hence disadvantageous from the viewpoint of cost.

In the practice of the present invention, the amount of preliminary culture solution inoculated into a culture medium for main cultivation is not less than 5% by volume. If the amount is less than 5% by volume, the initial amount of microbial cells present in the culture medium for main cultivation is so small that the growth thereof may be retarded to cause a reduction in the productivity of xanthan gum.

In the production of xanthan gum by fermentation, the agitating speed of the helical impeller and the turbine impeller within the fermenter (which is generally equal to the rotational speed of the agitator shaft) is controlled in such a way that the impellers are rotated at a low speed in the early stage of the fermentation and their agitating speed is increased with the increase in viscosity due to the formation of xanthan gum. High-speed agitation in the early stage of the fermentation is disadvantageous from the viewpoint of power consumption for agitation.

After completion of the fermentation, the microbial cells are killed (e.g., by heat treatment). Then, xanthan gum is precipitated by mixing the fermented solution with a hydrophilic organic solvent incapable of dissolving xanthan gum. Specific examples of such hydrophilic organic solvents include alcohols (such as isopropanol), acetone and the like, as well as aqueous solutions thereof.

Thereafter, the recovered xanthan gum is dried. This drying is carried out in an air dryer or a vacuum dryer at 40–100° C. for 2 hours or more.

As is evident from the above description, the present invention provides apparatus an method for the production of a polysaccharide which can realize a satisfactorily aerated and mixed state and thereby yield xanthan gum with high productivity even in the high-viscosity period corresponding to the late stage of the cultivation. As pointed out, while the primary description has been provided in the context of xanthan gum production, the apparatus and process of the invention is suitable for use with any biopolymer or polysaccharide which exhibits the same properties and variation in properties during the progress of the polymerization. e.g., need for increased aeration in the early stages of the reaction and need for enhanced thermal transfer during the latter stages of the reaction when the viscosity has increased due to the increased concentration of product.

More specifically, as a result of the combined use of a helical impeller and a turbine impeller in accordance with the present invention, the high shearing force of the turbine impeller can maintain an appropriate dissolved oxygen level required for the growth of microbial cells in the early stage of the fermentation, whereas the helical impeller can effectively agitate the highly viscous fermented solution after its viscosity has increased owing to the formation of product, e.g., xanthan gum.

Thus, the production of a polysaccharide by fermentation can be carried out without causing a reduction in the formation rate of a polysaccharide even in the late stage of the fermentation. Moreover, high productivity can be achieved at lower power consumption as compared with conventional cases in which a turbine impeller is used alone or in combination with a pitched-blade impeller.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 illustrates an outline of the apparatus for the production of a polysaccharide in accordance with the present invention.

As seen in this figure, the apparatus 1 for the production of a polysaccharide consists of a fermenter 2, an helical impeller unit 3 comprising a first upper helical impeller 3', a second helical impeller 3" positioned adjacent and immediately below the first helical impeller and a lower turbine impeller 4 spaced apart from and positioned below the helical impeller unit, all of which are secured to a shaft 5 positioned vertically and centrally within fermenter 2. While this preferred embodiment depicts a helical impeller having two impeller units, it is possible to use one such unit, or if desired, three or more, depending on the particular polymerization being carried out and the size of the fermenter and other equipment.

The aforesaid fermenter 2 has therewithin an aqueous culture medium 6 containing a polysaccharide producing microorganism, at least a carbohydrate source and a nitrogen source.

In this embodiment, the upper helical impeller 3 and the lower turbine impeller 4 are attached to the common agitator shaft 5.

In FIG. 1, numeral 7 designates as a motor serving as a means for driving agitator shaft 5 and numeral 8 designates a mechanical seal.

Figure 2:
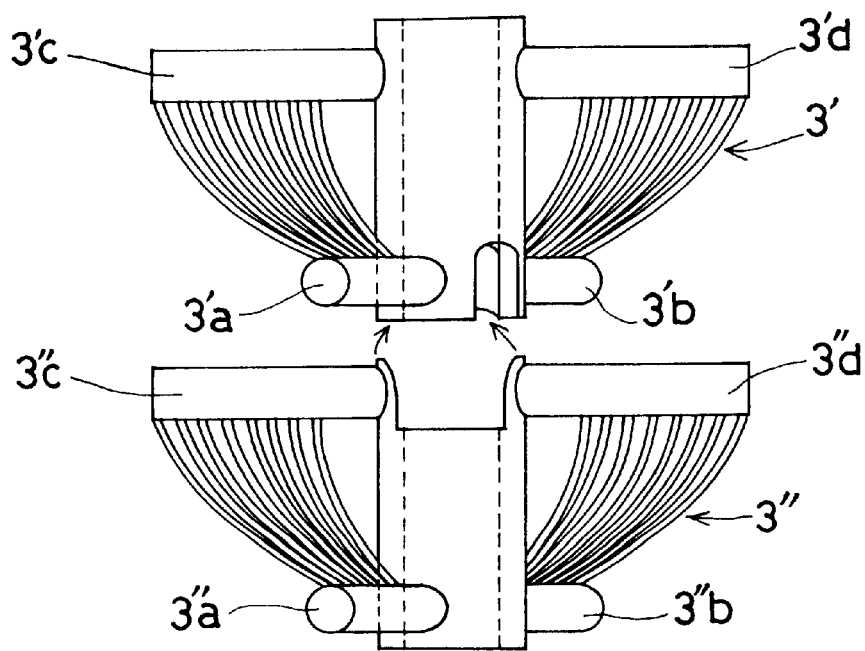
FIG. 2 is an exploded view of the inventive agitator of FIG. 1.
Figure 3:
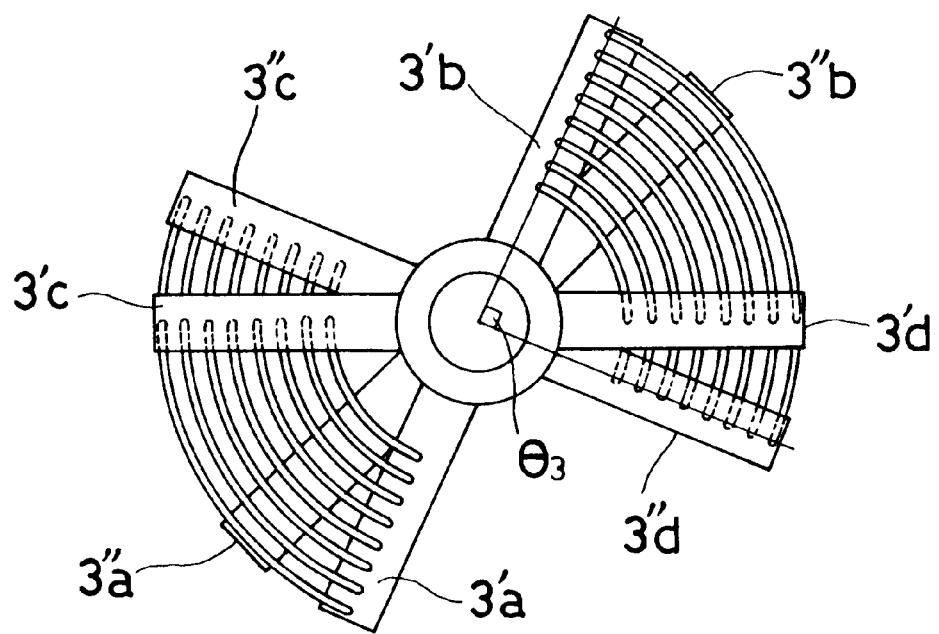
FIG. 3 is a plane view from above of the agitator of FIG. 2.

FIGS. 2 and 3 show additional views of the impeller unit 3 of FIG. 1. As shown in FIG. 2, impeller 3' has bottom opposing arms 3'$a$ and 3'$b$ and lower helical impeller 3" has upper opposing arms 3"$c$ and 3"$d$. The helical impellers 3' and 3" are interlocked as shown one on top of the other, such that the combination of arms 3'$a$ and 3'$b$ are situated at right angle to arm 3"$c$ and 3"$d$. This is depicted in FIG. 3 representing a plane view from the top looking down upon the impeller units of FIG. 2. As shown therein, the combination of impeller units 3'$a$ and 3'$b$ are at a right angle $\theta_3$ to the combination of impeller units 3"$c$ and 3"$d$. The relative positions of units 3'$c$, 3'$d$, 3"$a$, and 3"$b$ are also shown.

Figure 4:
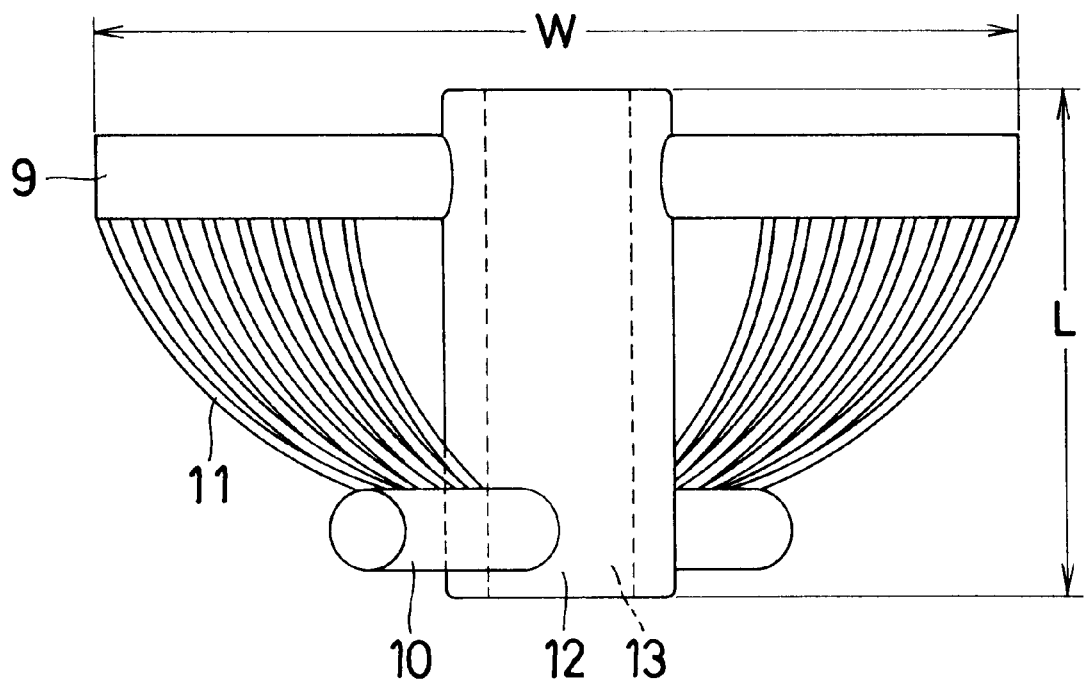
FIGS. 4 and 5 are side and bottom views, respectively, of a helical impeller for use in the apparatus for the production of a polysaccharide in accordance with the present invention, the helical impeller being used in Testing Examples 1 and 8.
Figure 5:
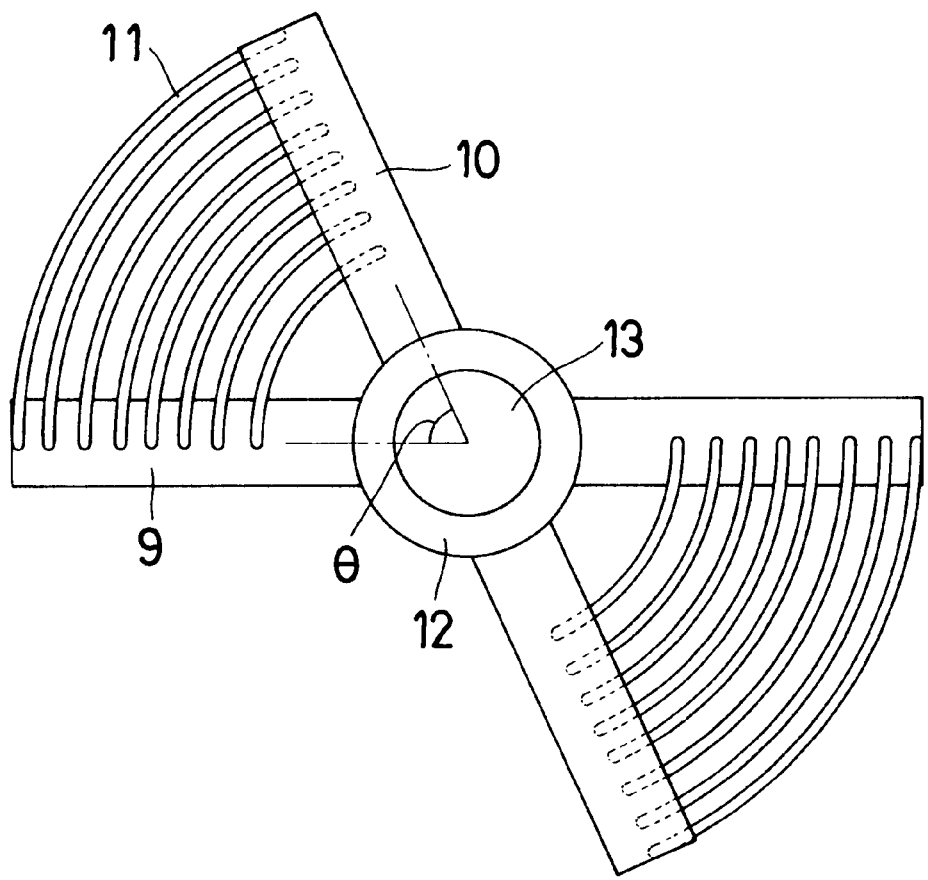

As illustrated in FIGS. 4 and 5, helical impeller 3 consists of a pair of vertically spaced cylindrical arms 9 and 10 extending in opposite directions from agitator shaft 5 and arranged in twisted relationship, and eight shearing paddles 11 bridging these arms 9 and 10. Numeral 12 designates a sleeve to which arms 9 and 10 are attached, and helical impeller 3 is fixed to agitator shaft 5 by inserting agitator shaft 5 into the central bore 13 of this sleeve 12.

With this helical impeller, the ratio of the impeller diameter to the tank diameter (of the fermenter) is 0.77, and the ratio of the impeller length (L) to the impeller diameter (W) is 0.40.

The angle of twist ($\theta$) between the upper and lower arms is 65.5 degrees.

Figure 6:
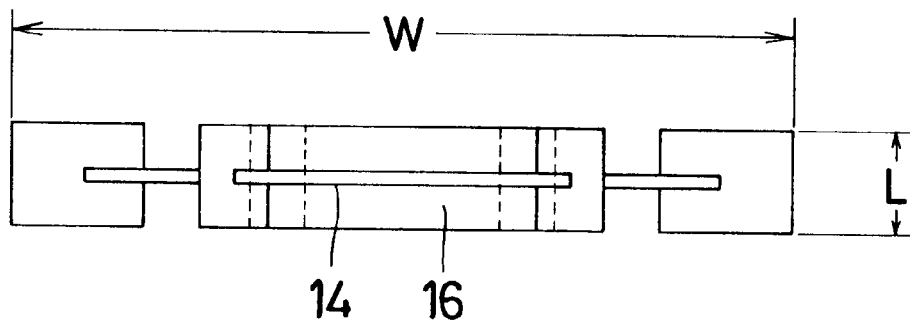
FIGS. 6 and 7 are side and bottom views, respectively, of a turbine impeller for use in the apparatus for the production of a polysaccharide in accordance with the present invention, the turbine impeller being used in various testing examples and comparative examples.
Figure 7:
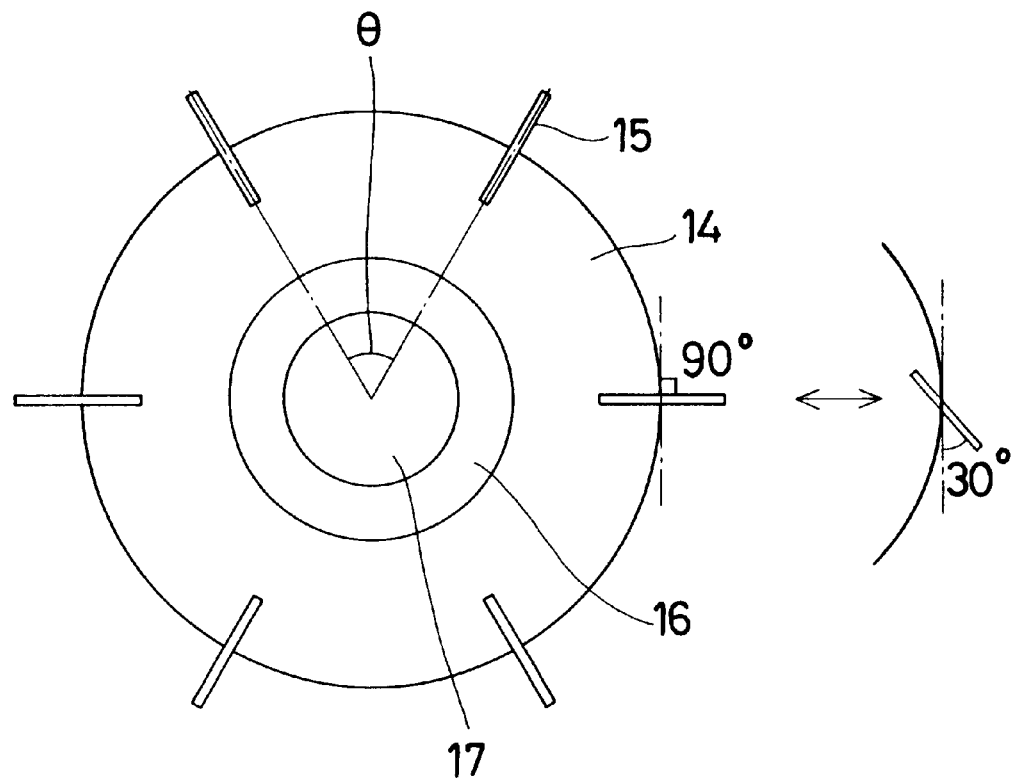
Figure 8:
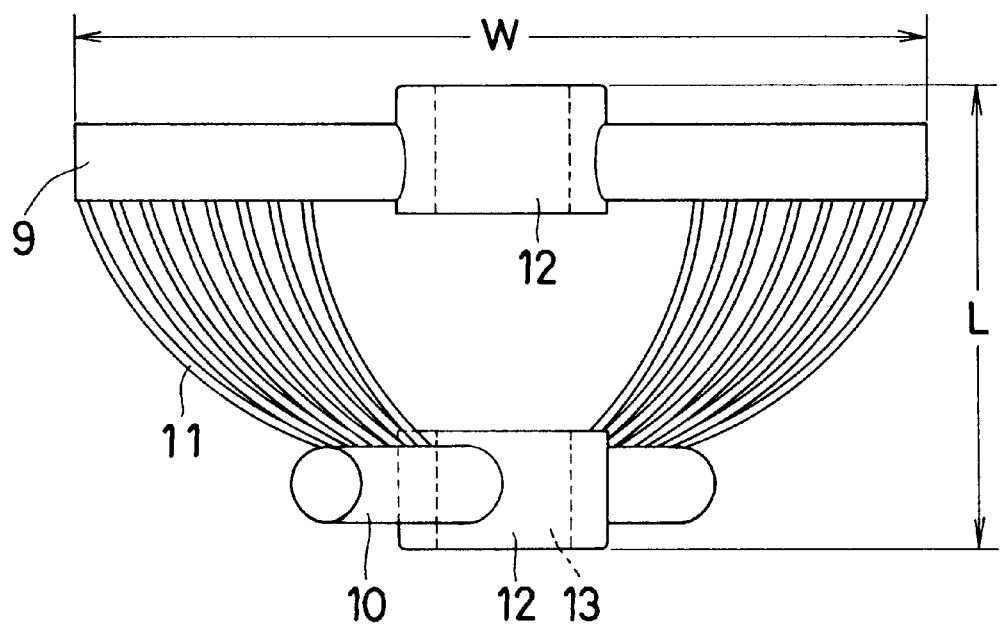
FIGS. 8 and 9 are side and bottom views, respectively, of another helical impeller for use in the apparatus for the production of a polysaccharide in accordance with the present invention, the helical impeller being used in Testing Examples 2, 4, 9 and 11.

FIGS. 6 and 7 illustrate turbine impeller 4. Turbine impeller 4 consists of a rotating disc 14 having six turbine blades 15 attached thereto. Numeral 16 designates a sleeve to which rotating disc 14 is attached, and turbine impeller 4 is fixed to agitator shaft 5 by inserting agitator shaft 5 into the central bore 17 of this sleeve 16.

With this turbine impeller, the ratio of the impeller diameter to the tank diameter (of the fermenter) is 0.50.

The turbine blades 15 may have any suitable shape, e.g., triangular, rectangular, pentagonal, and the like. The blades may be positioned at an angle relative to the circumferential point of attachment of disc 14 between 30 to 90 degrees. If the angle is less than about 30 degrees, the shearing force will be too low resulting in insufficient foam dispersion.

Figure 7A:
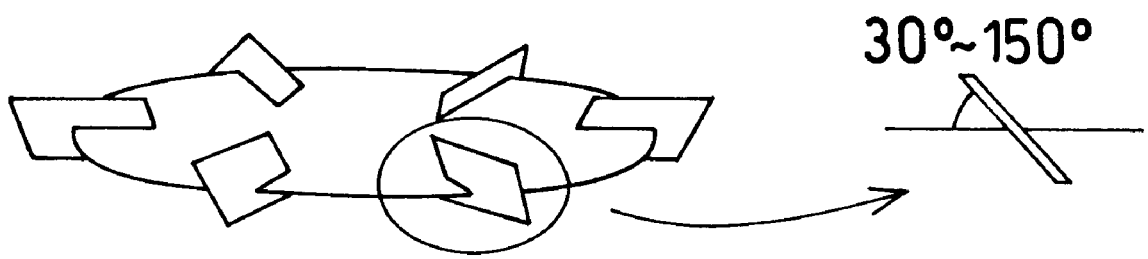
FIG. 7A is a side view of a helical impeller for use in the apparatus for the production of a polysaccharide in accordance with the present invention.
Figure 9:
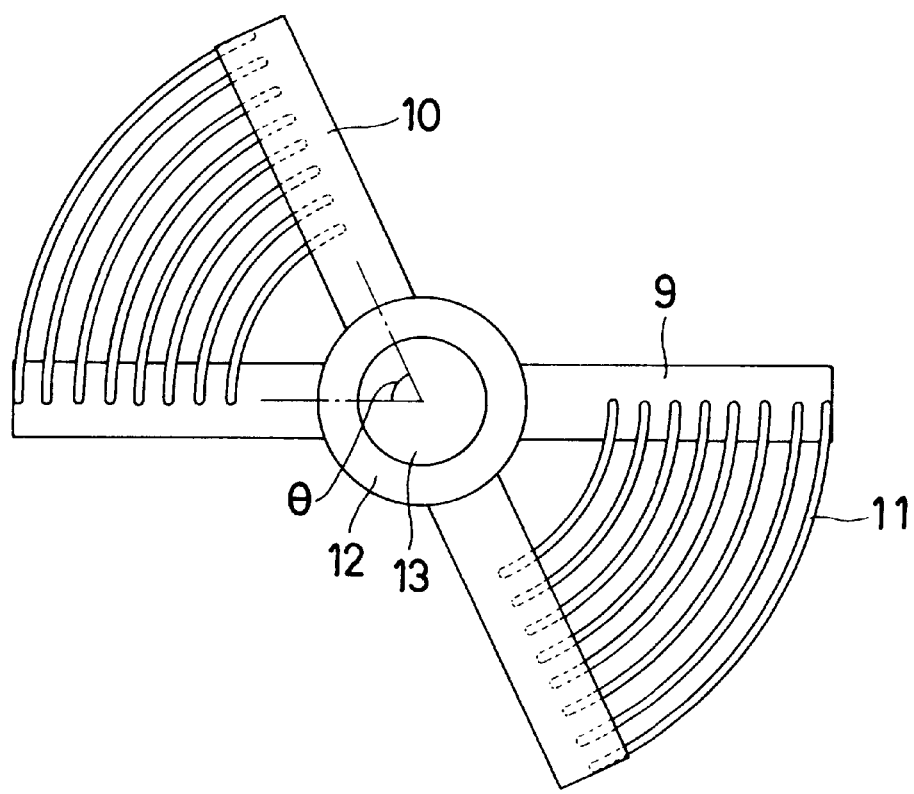
Figure 10:
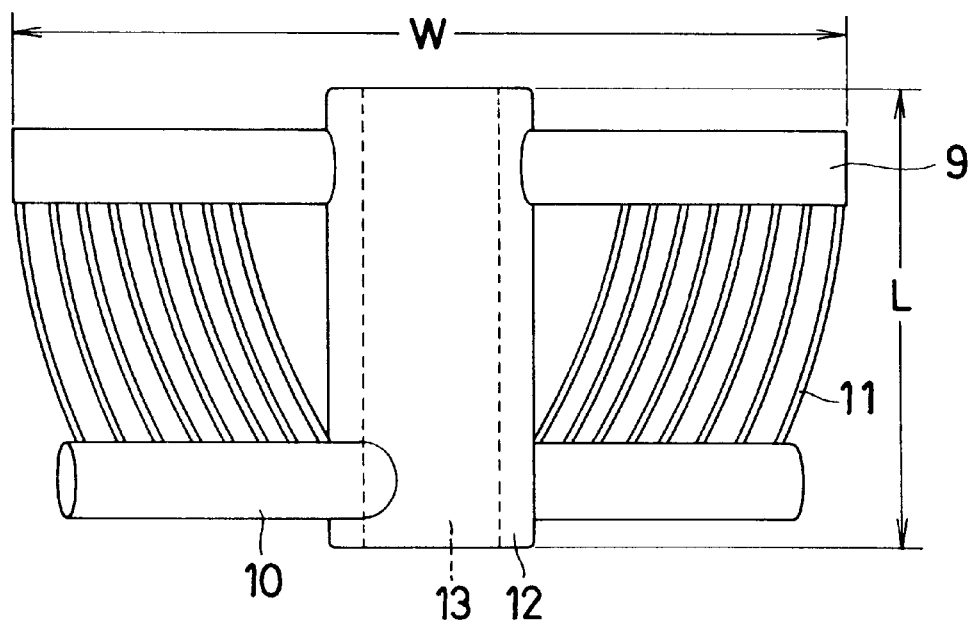
FIGS. 10 and 11 are side and bottom views, respectively, of still another helical impeller for use in the apparatus for the production of a polysaccharide in accordance with the present invention, the helical impeller being used in Testing Examples 3 and 10.
Figure 11:
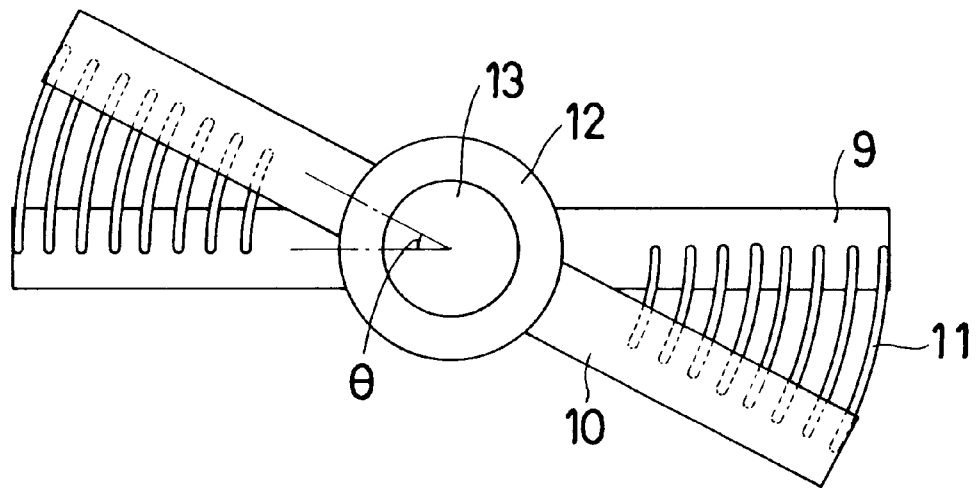
Figure 12:
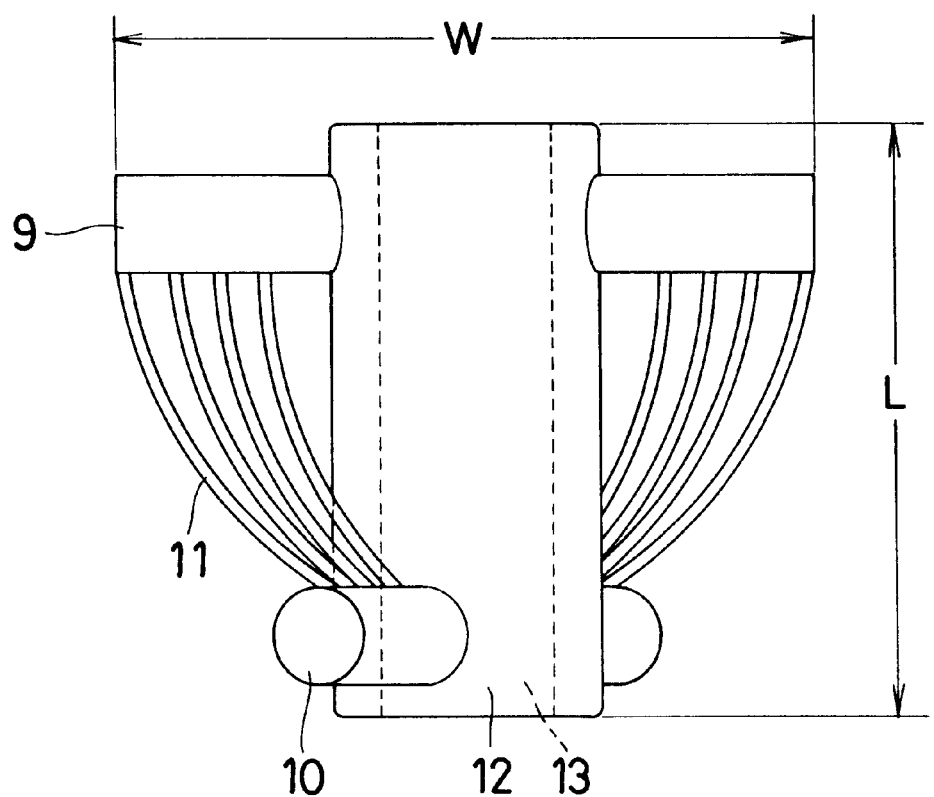
FIGS. 12 and 13 are side and bottom views, respectively, of a further helical impeller for use in the apparatus for the production of a polysaccharide in accordance with the present invention, the helical impeller being used in Testing Examples 5 and 12.
Figure 13:
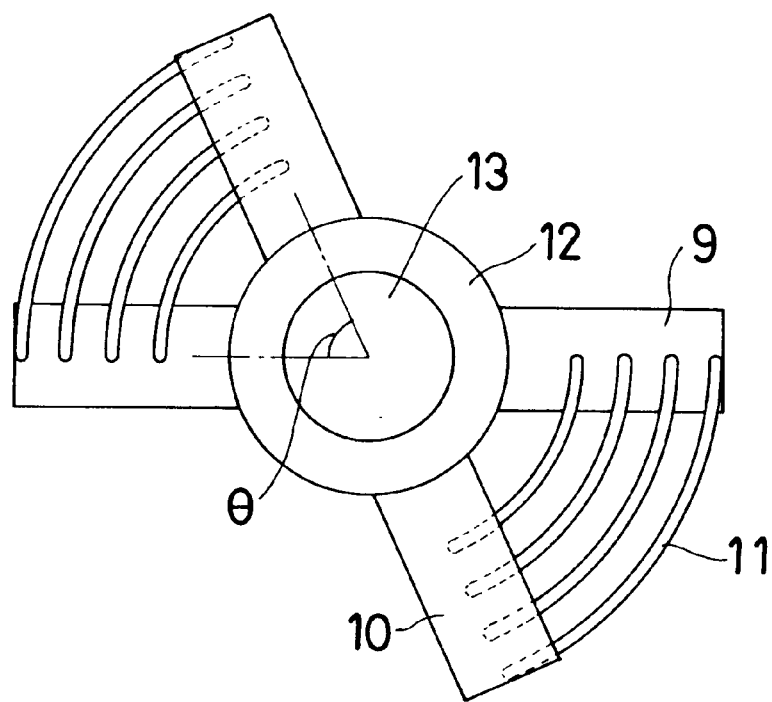
Figure 14:
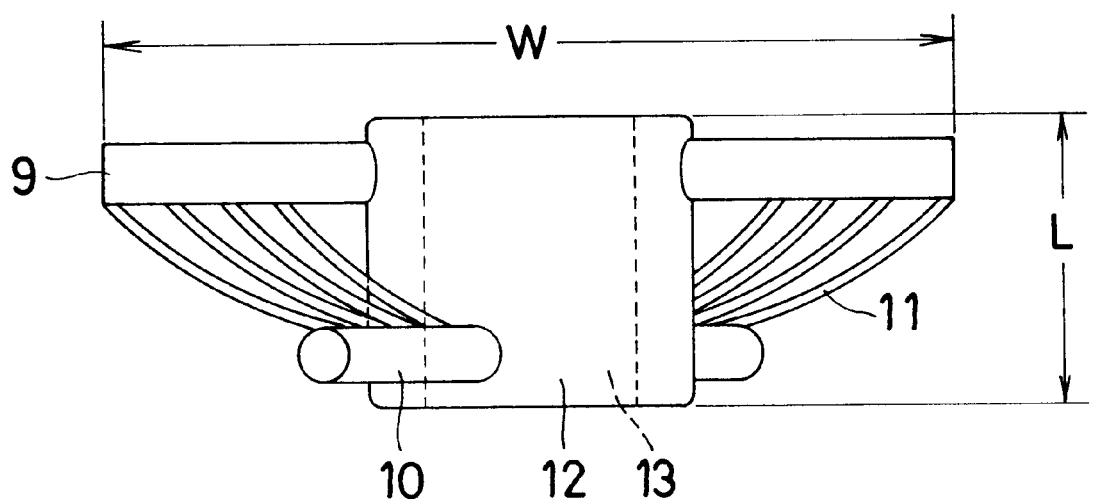
FIGS. 14 and 15 are side and bottom views, respectively, of a still further helical impeller for use in the apparatus for the production of a polysaccharide in accordance with the present invention, the helical impeller being used in Testing Examples 6 and 13.
Figure 15:
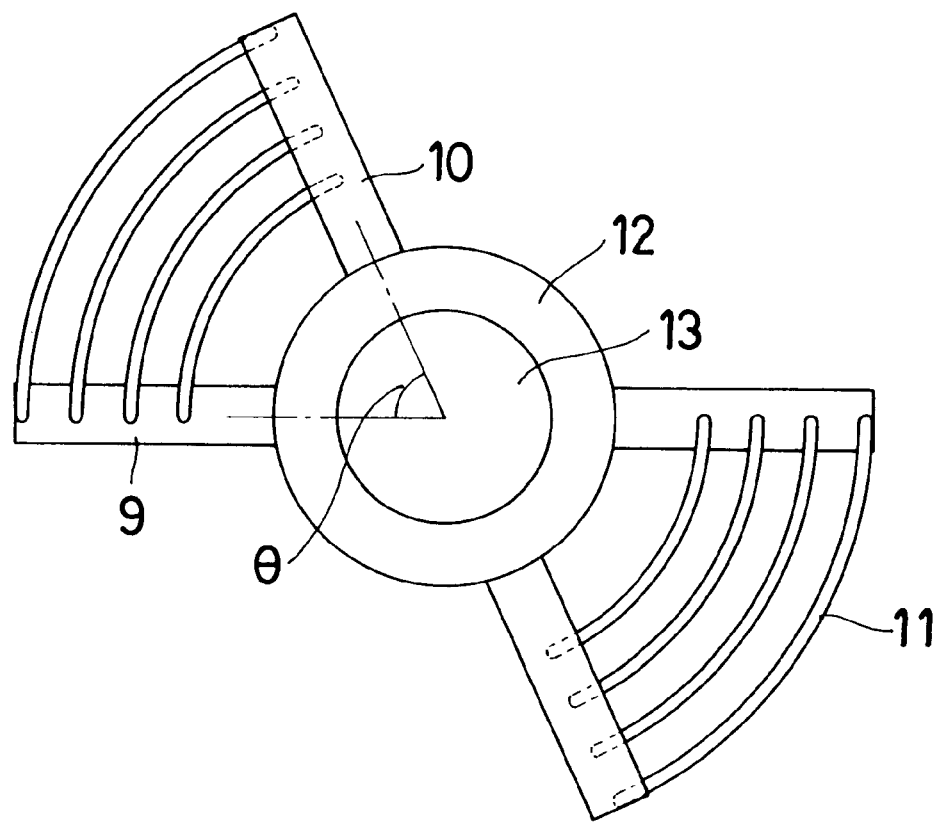
Figure 16:
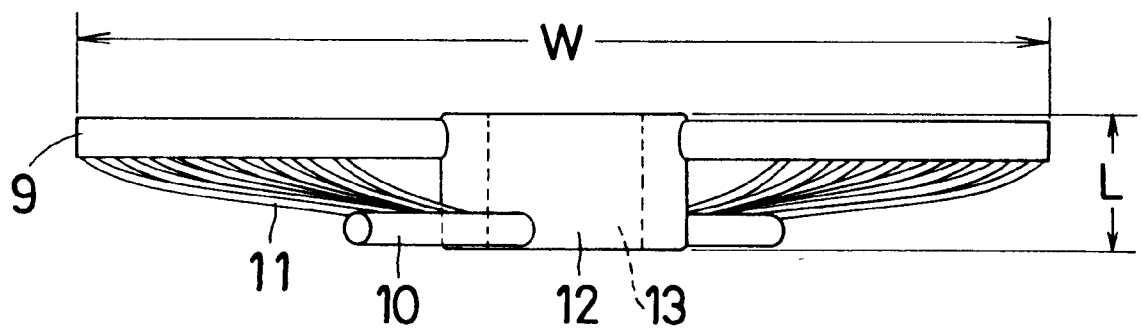
FIGS. 16 and 17 are side and bottom views, respectively, of a helical impeller used in Comparative Examples 1 and 7.
Figure 17:
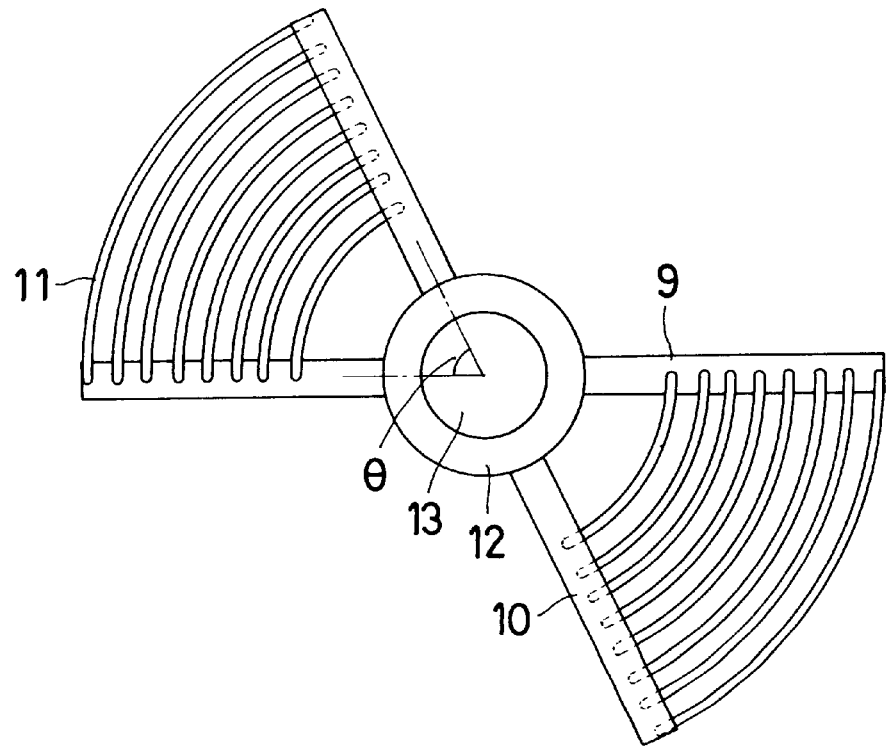
Figure 18:
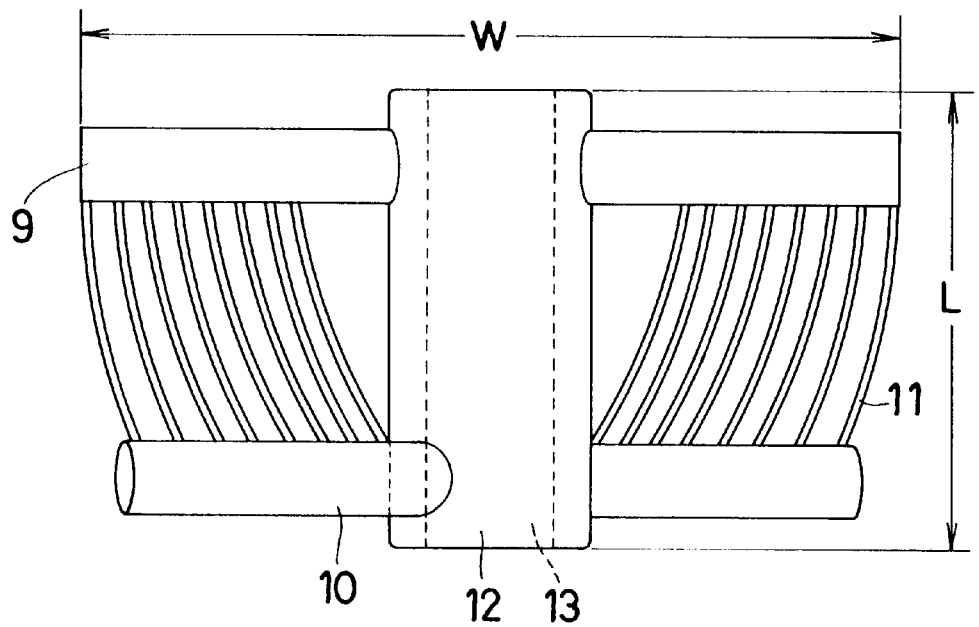
FIGS. 18 and 19 are side and bottom views, respectively, of a helical impeller used in Comparative Examples 2 and 8.
Figure 19:
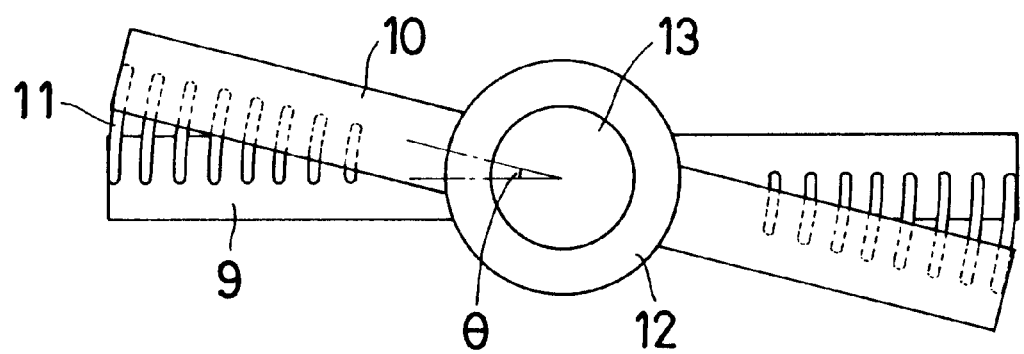
Figure 20:
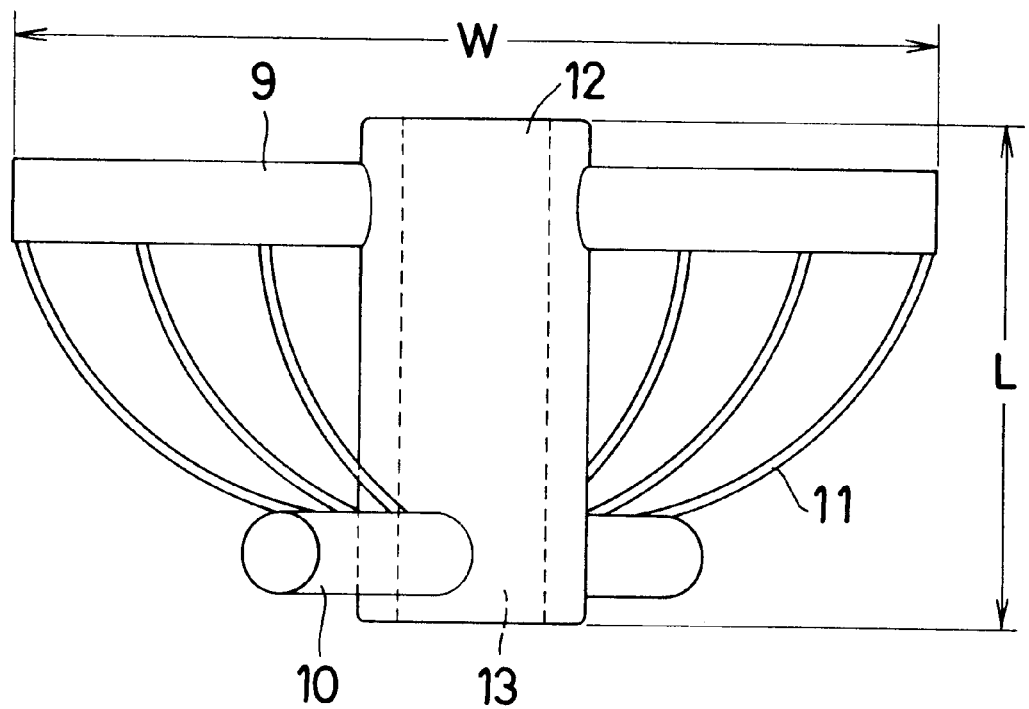
FIGS. 20 and 21 are side and bottom views, respectively, of a helical impeller used in Comparative Examples 3 and 9.
Figure 21:
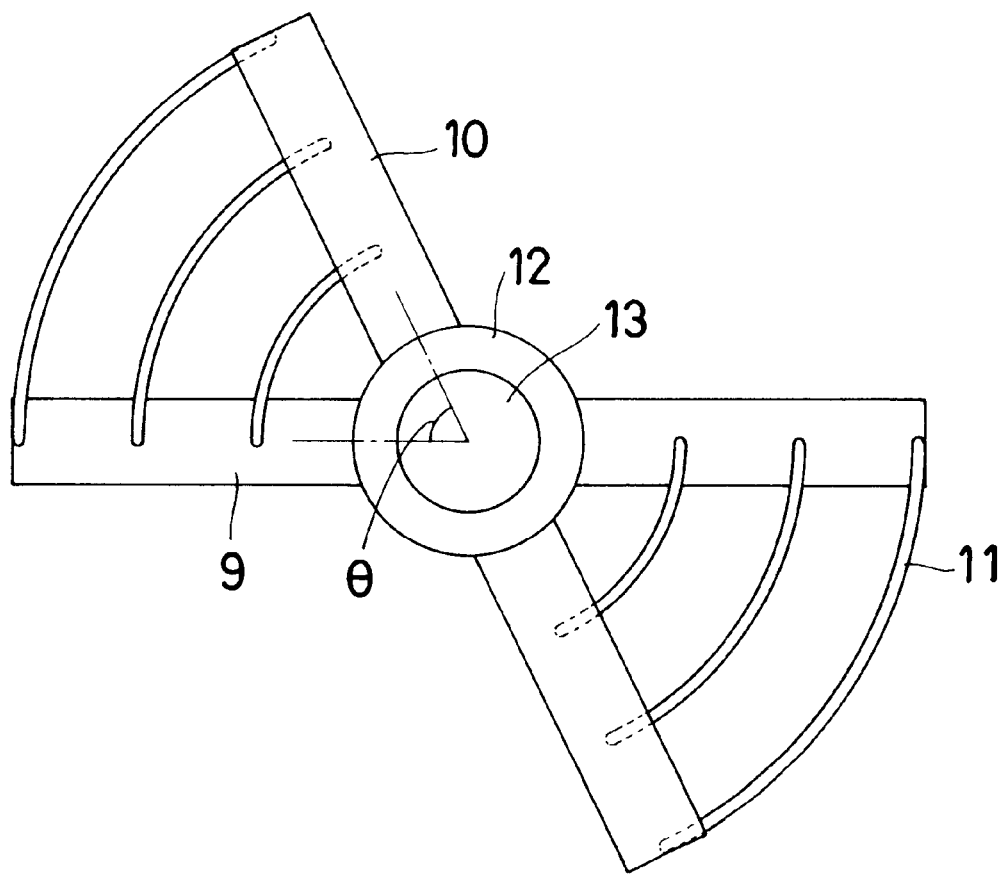

As shown in FIG. 7, also as shown in FIG. 7A, the blades may be angled relative to the plane of the disc of from about 30 to 150 degrees. If the angle is not within this range, the shearing force will be too low resulting in insufficient foam dispersion.

In the apparatus for the production of a polysaccharide in accordance with the above-described embodiment, agitation within fermenter 2 is carried out by rotating helical impeller 3 and turbine impeller 4 through rotation of agitator shaft 5. During this agitation, the broth is shorn by the shearing paddles of helical impeller 3, thus causing a reduction in the apparent viscosity of the highly viscous broth. Moreover, since the shearing paddles are tilted, good mass transfer within the fermenter can be maintained by producing a vertical flow efficiently within the fermenter.

The above-described helical impeller 3 can be modified in various ways by altering its dimensions. Moreover, the number of impeller units is not limited to 2, and a single impeller unit or more then two impeller units may be used.

FIGS. 8 to 15 illustrate several modifications thereof, which are used in various testing examples which will be given later. In this connection, FIGS. 6 and 7 illustrates the type of helical impeller in which sleeve 12 is divided into upper and lower parts.

Figure 22:
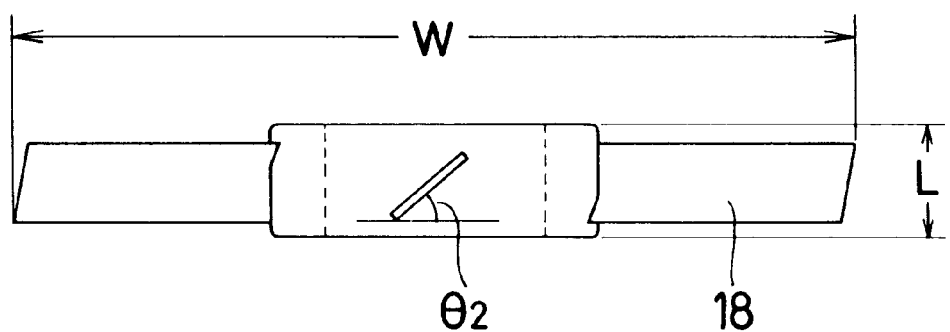
FIGS. 22 and 23 are side and bottom views, respectively, of a pitched-blade impeller used in Comparative Examples 4, 5, 10 and 11.
Figure 23:
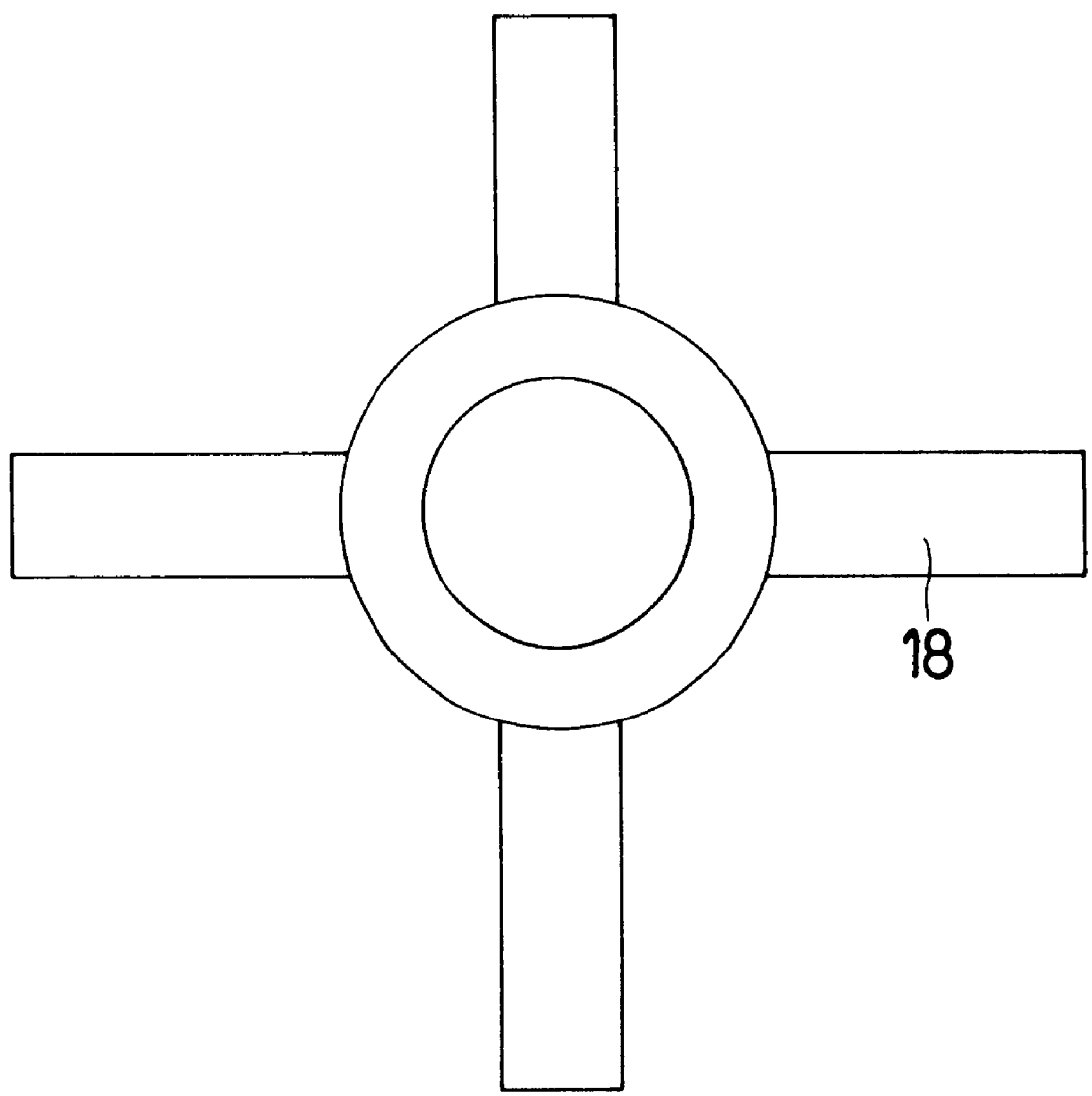

The impellers illustrated in FIGS. 16 to 23 are those used in comparative examples. FIGS. 22 and 23 illustrates a pitched-blade impeller in which the agitating blades 18 have an angle of inclination (θ2) of 45 degrees.

It is to be understood that the apparatus for the production of a polysaccharide in accordance with the present invention can be otherwise modified in various ways, and it is intended to cover in the appended claims all such changes and modifications as fall within the true spirit and scope of the invention.

For example, it is possible to rotate the helical impeller and the turbine impeller at different speeds by using any well-known means.

However, it is preferable to satisfy the following conditions. With the helical impeller, the ratio of the impeller diameter to the tank diameter (of the fermenter) should preferably be not less than 0.5. If the ratio is less than 0.5, a dead region is formed within the fermenter to cause a reduction in fermentation productivity.

With the helical impeller, the ratio of the impeller length to the impeller diameter should preferably be not less than 0.2. If the ratio is less than 0.2, the number of impeller units must be increased in order to achieve the same degree of agitation, resulting in a greater amount of power consumption.

The angle of twist between the upper and lower arms should preferably be not less than 20 degrees and not more than 180 degrees. If the angle of twist is less than 20 degrees, a sufficient vertical flow is not obtained, resulting in a reduction in productivity. If the angle of twist is greater than 180 degrees, it is difficult to maintain the shape of the paddles when the agitation is carried out.

It is preferable that the helical impeller be provided with four or more shearing paddles. If the number of shearing paddles is less than 4, a sufficient shearing force is not obtained. No particular limitation is placed on the width of the shearing paddles. With the turbine impeller used in the present invention, the ratio of the impeller diameter to the tank diameter (of the fermenter) should preferably be not less than 0.3. If the ratio is less than 0.3, the solubility of oxygen injected from a sparger is so low as to cause a reduction in productivity.

With the turbine impeller, the ratio of the impeller spacing to the impeller diameter should preferably be not greater than 1. If the ratio is greater than 1, the impeller spacing is so wide that a dead region is formed to cause a reduction in fermentation productivity. As used herein, impeller spacing means the distance from the bottom of the upper helical impeller to the top of the lower turbine impeller as shown in FIG. 1 by the letter "D".

In the following Testing Examples 1–6, xanthan gum was produced by using the impellers explained in connection with the above-described embodiments. The results thus obtained are shown below. In order to clarify the differences from the prior art, the results of Comparative Examples 1–6 are also shown.

Testing Examples 1–6

*Xanthomonas campestris* was cultivated for 24 hours in a fermenter containing a culture medium having the composition I given below, and then inoculated into a 30-liter fermenter containing a culture medium having the composition II given below. Then, fermentation was carried out by using various impellers having the shapes explained in connection with the above-described embodiments. The parameters of these impellers and their manner of mounting are shown in Table 1.

| I. Composition of a culture medium for preliminary cultivation | |
|---|---|
| Glucose | 5.8 g/L |
| Polypeptone | 5.2 g/L |
| Yeast extract | 2.6 g/L |
| NaCl | 9.0 g/L |
| Water | 1.8 L |
| II. Composition of a culture medium for main cultivation | |
| Glucose | 58 g/L |
| Soybean powder | 3.3 g/L |
| (Nitrogen content | 0.3 g/L) |
| $KH_2PO_4$ | 2.0 g/L |
| $MgSO_4 - 7H_2O$ | 0.5 g/L |
| Water | 16.2 L |

TABLE 1

| Testing Example No. | | Example 1 | Example 2 | Example 3 | Example 4 | Example 5 | Example 6 |
|---|---|---|---|---|---|---|---|
| FERMENTER | Tank diameter (mm) | 260.0 | 260.0 | 260.0 | 260.0 | 260.0 | 260.0 |
| | Tank length (mm) | 575.6 | 575.6 | 575.6 | 575.6 | 575.6 | 575.6 |
| Type of impeller | | | | | | | |
| Helical Impeller | Impeller diameter/tank diameter | 0.77 | 0.77 | 0.77 | 0.77 | 0.50 | 0.50 |
| | Impeller length/impeller diameter | 0.40 | 0.40 | 0.40 | 0.40 | 0.62 | 0.25 |
| | Number of shearing paddles | 8 | 8 | 8 | 8 | 4 | 4 |
| | Number of impeller units | 2 | 2 | 2 | 2 | 2 | 2 |
| | Angle of twist (degrees) | 65.5 | 65.5 | 20 | 65.5 | 65.5 | 65.5 |
| | Shape of impeller (FIGS) | 4 5 | 8 9 | 10 11 | 8 9 | 12 13 | 14 15 |
| Turbine impeller | Impeller diameter/tank diameter | 0.50 | 0.50 | 0.50 | 0.30 | 0.50 | 0.50 |
| | Number of impeller units | 1 | 1 | 1 | 1 | 1 | 1 |
| Impeller spacing/impeller diameter | Helical impeller | 0.00 | 0.00 | 0.00 | 0.00 | 0.00 | 0.73 |
| | Turbine impeller | 0.80 | 0.80 | 0.80 | 0.80 | 0.80 | 0.80 |
| Maximum rotational speed (rpm) | | 800 | 600 | 800 | 600 | 800 | 800 |

After fermentation was carried out for 2 days under the above-described conditions, the microbial cells were killed by heating the fermented solution at 70° C. for an hour. Thereafter, using a mixer, xanthan gum was precipitated with the aid of 1.5 parts by weight of an 85% aqueous solution of IPA. The precipitated xanthan gum was recovered, dried at 60° C. for 3 hours by means of an air dryer, and then weighed.

The final viscosity of the fermented solution, residual glucose concentration, xanthan gum concentration and final power consumption, which were observed in each testing example, are shown in Table 2. The viscosity was measured at 20° C. with a BL Viscometer (manufactured by Tokimec Inc.; rotor No. 4, 30 rpm).

The residual glucose concentration was measured with an Enzyme Electrode Analyzer M-100 (manufactured by Asahi Chemical Industry Co., Ltd.).

It was confirmed that satisfactory production of xanthan gum could be achieved even at a low agitating speed equal to that employed in Comparative Example 5 given later. Thus, the helical impeller was found to be capable of effecting good mass transfer.

Testing Example 7

After fermentation was carried out for 2 days under the same conditions as in Testing Example 1, 500 ml of an aqueous solution containing 414 g of glucose was sterilized and added to the fermenter. Thereafter, the fermentation was continued for an additional 1 day. The results thus obtained are shown in Table 3.

It was confirmed that the helical impeller permitted satisfactory production of xanthan gum even at a viscosity of 30,000 cP.

TABLE 2

| Testing Example | Example 1 | Example 2 | Example 3 | Example 4 | Example 5 | Example 6 |
|---|---|---|---|---|---|---|
| Final viscosity of fermented solution (CP) | 20000 | 19000 | 20000 | 18000 | 17500 | 18000 |
| Residual glucose concentration (g/L) | 0 | 0 | 0 | 0 | 0 | 0 |
| Xanthan gum concentration (g/L) | 37 | 35 | 36 | 38 | 35 | 33 |
| Final power consumption (kw) | 0.9 | 0.7 | 0.9 | 0.9 | 0.7 | 0.7 |

TABLE 3

| Testing Example No. | Example 7 |
|---|---|
| Final viscosity of fermented solution (cP) | 30000 |
| Residual glucose concentration (%) | 0 |
| Xanthan gum concentration (%) | 42 |
| Final power consumption (kw) | 1.0 |

COMPARATIVE EXAMPLES 1–6

Fermentation was carried out by using the same culture medium as in the testing examples and various impellers shown in Table 4.

It can be seen from a comparison of the above-described testing examples and comparative examples that the present invention brings about a significant improvement in productivity.

In the following Testing Examples 8–13, macromolecular *pullulan* was produced by using the impellers explained in connection with the above-described embodiments. The results thus obtained are shown below. In order to clarify the The conditions employed are shown in Table 4, and the results thus obtained are shown in Table 5.

TABLE 4

| Testing Example No. | | Example 1 | Example 2 | Example 3 | Example 4 | Example 5 | Example 6 |
|---|---|---|---|---|---|---|---|
| FERMENTER | Tank diameter (mm) | 260.0 | 260.0 | 260.0 | 260.0 | 260.0 | 260.0 |
| | Tank length (mm) | 575.6 | 575.6 | 575.6 | 575.6 | 575.6 | 575.6 |
| Type of impeller | | | | | | | |
| Upper Impeller | Impeller diameter/tank diameter | 0.77 | 0.77 | 0.77 | 0.50 | 0.50 | 0.50 |
| | Impeller length/impeller diameter | 0.10 | 0.40 | 0.40 | 0.015 | 0.015 | 0.015 |
| | Number of shearing paddles | 8 | 8 | 3 | — | — | — |
| | Number of impeller units | 2 | 2 | 2 | 2 | 2 | 2 |
| | Angle of twist (degrees) | 65.5 | 15 | 65.5 | — | — | — |
| | Shape of impeller (FIGS) | 16 17 | 18 19 | 20 21 | 22 23 | 22 23 | 6 7 |
| Turbine impeller | Impeller diameter/tank diameter | 0.50 | 0.50 | 0.50 | 0.50 | 0.50 | 0.50 |
| | Number of impeller units | 1 | 1 | 1 | 1 | 1 | 1 |
| Impeller spacing/impeller diameter | Upper impeller | 0.71 | 0.00 | 0.00 | 0.71 | 0.71 | 0.71 |
| | Turbine impeller | 0.80 | 0.80 | 0.80 | 0.80 | 0.59 | 0.59 |
| Maximum rotational speed (rpm) | | 800 | 800 | 800 | 800 | 600 | 800 |

TABLE 5

| Comparative Example No. | Comp. Example 1 | Comp. Example 2 | Comp. Example 3 | Comp. Example 4 | Comp. Example 5 | Comp. Example 6 |
|---|---|---|---|---|---|---|
| Final viscosity of fermented solution (cP) | 12000 | 11000 | 12000 | 18000 | 10500 | 1500 |
| Residual glucose | 5 | 8 | 10 | 0 | 15 | 5 |
| Xanthan gum concentration (g/L) | 28 | 24 | 24 | 36 | 22 | 29 |
| Final power consumption (kw) | 0.8 | 0.8 | 0.9 | 0.9 | 0.7 | 0.9 | differences from the prior art, the results of Comparative Examples 7–12 are also shown.

Testing Examples 8–13

*Aureobasidium pullulans* (ATCC74105) was cultivated for 24 hours in a fermenter containing a culture medium having the composition I given below, and then inoculated into a 30 liter fermenter containing a culture medium having the composition II given below. The fermentation was carried out by using various impellers having the shapes illustrated in the figures attached hereto. The parameters of these impellers and their manner of mounting are shown in Table 6.

| I. Composition of a culture medium for preliminary cultivation. | |
|---|---|
| Sucrose | 10.0 g/L |
| Yeast extract F | 2.0 g/L |
| $(NH_4)_2SO_4$ | 0.5 g/L |
| $K_2HPO_4$ | 3.0 g/L |
| $MgSO_4 \cdot 7H_2O$ | 0.2 g/L |
| $FeSO_4 \cdot 7H_2O$ | 0.01 g/L |
| $MnSO_4 \cdot 7H_2O$ | 0.01 g/L |
| $ZnSO_4 \cdot 7H_2O$ | 0.01 g/L |
| Water | 2.5 L |
| pH | 7.0 |
| II. Composition of a culture medium for main cultivation | |
| Sucrose | 100.0 g/L |
| $(NH_4)_2SO_4$ | 1.0 g/L |
| $K_2HPO_4$ | 2.0 g/L |
| $FeSO_4 \cdot 7H_2O$ | 0.01 g/L |
| $MnSO_4 \cdot 7H_2O$ | 0.01 g/L |
| $ZnSO_4 \cdot 7H_2O$ | 0.01 g/L |
| Water | 16.2 L |
| pH | 7.0 | by heat treatment at 60° C. for 60 minutes while mechanically agitating. Then the cells were removed by a centrifuge. The *pullulan* solution thus obtained was mixed with 1.5 parts by weight of an 86% aqueous solution of IPA, to recover *pullulan* from the solution.

The final viscosity of the fermented solution, residual sucrose concentration, *pullulan* concentration, *pullulan* molecular weight and final power consumption, which were observed under the various fermenting conditions, are shown in Table 7. The viscosity was measured at 20° C. with a BL Viscometer (manufactured by Tokimec Inc., rotor No. 4, 30 rpm).

The residual sucrose concentration was measured with an Enzyme Electrode Analyzer M-100 (manufactured by Asahi Chemical Industry Co., Ltd.). The *pullulan* molecular weight was obtained by measuring the intrinsic viscosity and calculating the result of the measurement according to the following relational expression developed by Buliga et al. of intrinsic viscosity to molecular weight (Int. J. Biol. Macormol., Vol. 9, 71–76(1987)).

$$[\eta] = 0.000258 \times M_w^{0.646}$$

TABLE 6

| Testing Example No. | | Example 8 | Example 9 | Example 10 | Example 11 | Example 12 | Example 13 |
|---|---|---|---|---|---|---|---|
| FERMENTER | Tank diameter (mm) | 260.0 | 260.0 | 260.0 | 260.0 | 260.0 | 260.0 |
| | Tank length (mm) | 575.6 | 575.6 | 575.6 | 575.6 | 575.6 | 575.6 |
| Type of impeller | | | | | | | |
| Helical Impeller | Impeller diameter/tank diameter | 0.77 | 0.77 | 0.77 | 0.77 | 0.50 | 0.50 |
| | Impeller length/impeller diameter | 0.40 | 0.40 | 0.40 | 0.40 | 0.62 | 0.25 |
| | Number of shearing paddles | 8 | 8 | 8 | 8 | 4 | 4 |
| | Number of impeller units | 2 | 2 | 2 | 2 | 2 | 2 |
| | Angle of twist (degrees) | 65.5 | 65.5 | 20 | 65.5 | 65.5 | 65.5 |
| | Shape of impeller (FIGS) | 4 5 | 8 9 | 10 11 | 8 9 | 12 13 | 14 15 |
| Turbine impeller | Impeller diameter/tank diameter | 0.50 | 0.50 | 0.50 | 0.30 | 0.50 | 0.50 |
| | Number of impeller units | 1 | 1 | 1 | 1 | 1 | 1 |
| Impeller spacing/impeller diameter | Helical impeller | 0.00 | 0.00 | 0.00 | 0.00 | 0.00 | 0.73 |
| | Turbine impeller | 0.80 | 0.80 | 0.80 | 0.80 | 0.80 | 0.80 |
| Maximum rotational speed (rpm) | | 300 | 250 | 300 | 250 | 300 | 300 |

After fermentation was carried out for 5 days under the above-described conditions, the microbial cells were killed

TABLE 7

| Testing Example | Example 8 | Example 9 | Example 10 | Example 11 | Example 12 | Example 13 |
|---|---|---|---|---|---|---|
| Final viscosity of fermented solution (CP) | 13000 | 14000 | 14000 | 13000 | 12500 | 13000 |
| Residual sucrose concentration (g/L) | 0 | 0 | 0 | 0 | 0 | 0 |
| Pullulan concentration (g/L) | 56 | 58 | 58 | 56 | 55 | 56 |
| Molecular weight of pullulan ($\times 10^6$) | 6.5 | 6.4 | 6.8 | 6.3 | 6.6 | 6.5 |
| Final power consumption (kw) | 0.2 | 0.15 | 0.2 | 0.2 | 0.15 | 0.15 |

It was confirmed that satisfactory production of *pullulan* could be achieved even at a low agitating speed equal to that employed in Comparative Example 6 given later. Thus, the helical impeller was found to be capable of effecting good mass transfer.

COMPARATIVE EXAMPLES 7–12

Fermentation was carried out by using the same culture medium as in the testing examples and various impellers other than the helical impeller.

The conditions employed are shown in Table 8 and the results thus obtained are shown in Table 9.

TABLE 8

| Comparative Example No. | | Example 7 | Example 8 | Example 9 | Example 10 | Example 11 | Example 12 |
|---|---|---|---|---|---|---|---|
| FERMENTER | Tank diameter (mm) | 260.0 | 260.0 | 260.0 | 260.0 | 260.0 | 260.0 |
| | Tank length (mm) | 575.6 | 575.6 | 575.6 | 575.6 | 575.6 | 575.6 |
| Type of impeller | | | | | | | |
| Upper Impeller | Impeller diameter/tank diameter | 0.77 | 0.77 | 0.77 | 0.50 | 0.50 | 0.50 |
| | Impeller length/impeller diameter | 0.10 | 0.40 | 0.40 | 0.012 | 0.012 | 0.012 |
| | Number of shearing paddles | 8 | 8 | 3 | — | — | — |
| | Number of impeller units | 2 | 2 | 2 | 2 | 2 | 2 |
| | Angle of twist (degrees) | 65.5 | 15 | 65.5 | — | — | — |
| | Shape of impeller (FIGS) | 16 17 | 18 19 | 20 21 | 22 23 | 22 23 | 6 7 |
| Turbine impeller | Impeller diameter/tank diameter | 0.50 | 0.50 | 0.50 | 0.50 | 0.50 | 0.50 |
| | Number of impeller units | 1 | 1 | 1 | 1 | 1 | 1 |
| Impeller spacing/impeller diameter | Upper impeller | 0.71 | 0.00 | 0.00 | 0.71 | 0.71 | 0.71 |
| | Turbine impeller | 0.80 | 0.80 | 0.80 | 0.80 | 0.59 | 0.59 |
| Maximum rotational speed (rpm) | | 300 | 300 | 300 | 300 | 200 | 300 |

TABLE 9

| Composition Example | Example 7 | Example 8 | Example 9 | Example 10 | Example 11 | Example 12 |
| --- | --- | --- | --- | --- | --- | --- |
| Final viscosity of fermented solution (CP) | 8000 | 7000 | 8000 | 10000 | 5500 | 5500 |
| Residual sucrose concentration (g/L) | 5 | 8 | 10 | 0 | 15 | 5 |
| Pullulan concentration (g/L) | 40 | 35 | 40 | 50 | 28 | 29 |
| Molecular weight of pullulan ($\times 10^6$) | 6.5 | 6.6 | 6.8 | 6.4 | 6.3 | 6.1 |
| Final power consumption (kw) | 0.2 | 0.2 | 0.2 | 0.2 | 0.15 | 0.2 |

We claim:

1. An agitator for the production of polysaccharides by aerobic fermentation of a polysaccharide producing microorganism which comprises:

A. a shaft adapted for rotatable mounting in a fermentation chamber having disposed along is length, B. a helical impeller securable to the shaft comprising:
 (1) a first pair of arms, opposite one another and extending radially from the shaft in the same plane and in opposing directions,
 (2) a second pair of arms, opposite one another and extending radially from the shaft in the same plane and in opposing directions,
 the first and second pair of arms being spaced apart from each other along the length of the shaft and each extending from the shaft in a different radial direction from the other to define a radial angle therebetween; and
 (3) at least four shearing paddles connecting one arm of the first pair of arms to a corresponding arm of the second pair of arms and positioned in uniform spaced-apart relationship from one another along the lengths of the arm and corresponding arm, respectively; and C. a turbine impeller securable to the shaft at a distal position along the shaft length from the helical impeller, the turbine impeller comprising a rotatable disc having at least one turbine blade extending in a radial direction attached thereto.

2. The apparatus of claim 1 wherein the radial angle is at least 20 degrees.

3. The agitator according to claim 1 wherein the ratio of helical impeller length to helical impeller diameter is at least 0.2.

4. An apparatus for the production of polysaccharides by aerobic fermentation of a polysaccharide producing microorganism which comprises:

(A) a fermenter chamber for aerobic fermentation of a culture medium of the polysaccharide producing microorganism, (B) an agitator in the chamber, said agitator comprising:
 (1) a vertical shaft rotatably and axially mounted within the chamber,
 (2) drive means for rotating the shaft,
 (3) a helical impeller secured to the shaft within the fermenter, the helical impeller comprising:
  1. a first pair of arms, opposite one another and secured to and extending radially from the shaft in the same plane and in opposing directions,
  2. a second pair of arms, opposite one another and secured to and extending radially from the shaft in the same plane and in opposing directions,
  the first and second pair of arms being spaced apart from each other along the length of the shaft and each extending from the shaft in a different radial direction from the other to define a radial angle therebetween; and
   3. at least four shearing paddles connecting one arm of the first pair of arms to a corresponding arm of the second pair of arms and positioned in uniform spaced-apart relationship from one another along the lengths of the arm and corresponding arm, respectively; and
  (4) a turbine impeller secured to the shaft and positioned vertically below the helical impeller, the turbine impeller comprising a rotatable disc having at least one turbine blade extending in a radial direction attached thereto.

5. The apparatus of claim 4 wherein the radial angle is between about 20 to 180 degrees.

6. The apparatus of claim 5 wherein fermenter chamber is cylindrical and the ratio of the diameter of said helical impeller to the chamber diameter is at least 0.5.

7. The apparatus of claim 4, wherein the fermenter chamber is cylindrical and the ratio of the diameter of said turbine impeller to the chamber diameter is at least 0.3.

8. The apparatus according to claim 4 wherein the ratio of helical impeller length to helical impeller diameter is at least 0.2.

9. A method for the production of a polysaccharide comprising the steps of inoculating a polysaccharide-producing microorganism into an aqueous culture medium containing a carbohydrate source and a nitrogen source to produce a fermentation broth and subjecting the broth to aerobic fermentation conditions while mechanically agitating and aerating the broth using the apparatus as claimed in claim 1.

10. The method of claim 9 wherein the polysaccharide is xanthan gum or *pullulan*.

11. The method of claim 9 wherein the speed at which the impellers are rotated is increased during the fermentation as the viscosity of the fermentation liquid increases.

12. The method according to claim 9 wherein the ratio of helical impeller length to helical impeller diameter is at least 0.2.

* * * * *